United States Patent [19]

Davies

[11] Patent Number: 5,166,349
[45] Date of Patent: Nov. 24, 1992

[54] CHIRAL ORGANOIRON COMPLEXES AND USE FOR ASSYMETRIC REDUCTION

[75] Inventor: Stephen G. Davies, Oxford, England

[73] Assignee: The British Petroleum Company, p.l.c., London, England

[21] Appl. No.: 689,900

[22] PCT Filed: Nov. 1, 1990

[86] PCT No.: PCT/GB90/01674
§ 371 Date: Jun. 17, 1991
§ 102(e) Date: Jun. 17, 1991

[87] PCT Pub. No.: WO91/06550
PCT Pub. Date: May 16, 1991

[30] Foreign Application Priority Data

Nov. 2, 1989 [GB] United Kingdom ............... 8924736
Nov. 2, 1989 [GB] United Kingdom ............... 8924738
Nov. 2, 1989 [GB] United Kingdom ............... 8924740
Apr. 28, 1990 [GB] United Kingdom ............... 9009592
May 10, 1990 [GB] United Kingdom ............... 9010547

[51] Int. Cl.$^5$ .................. C07B 53/00; C07F 15/02
[52] U.S. Cl. ........................... 546/4; 560/60; 568/814; 568/881
[58] Field of Search ............. 560/60; 568/814, 881; 546/4

[56] References Cited

PUBLICATIONS

Brunner et al, Jour. of Organometallic Chem., vol. 210, No. 2, 1981, pp. 223-236.
Nakamura et al, *Tetrahedron Letters*, No. 48, 1978, Pergamon Press, pp. 4815-4818.
Davies et al, Tetrahedron Letters, vol. 11, No. 22, 1990 Pergamon Press, pp. 3213-3216.

*Primary Examiner*—Mark L. Berch
*Attorney, Agent, or Firm*—Nixon & Vanderhye

[57] ABSTRACT

Compounds having general formula (I) wherein (i) Cp is either a cyclopentadienyl ligand having the formula $C_5(R^3)_5$ where the $R^3$ groups are independently hydrogen, methyl or ethyl or an indenyl ligand; (ii) Z is a ligand having the formula $X(R^4)_2(Y)$ wherein X is selected from phosphorus, arsenic or antimony; the $R^4$ groups are independently aryl or aroxy and Y is selected from $-R^5-NHR^5$ and $-OR^5$ wherein $R^5$ is a hydrocarbyl group; (iii) the R groups are independently hydrogen, halogen or $C_1$ to $C_4$ alkyl; (iv) $R^1$ is selected from hydrogen, $C_1$ to $C_6$ alkyl, benzyl and $-CO_2R^6$ where $R^6$ is $C_1$ to $C_6$ alkyl; (v) $R^2$ is selected from hydrogen, $C_1$ to $C_{10}$ alkyl, phenyl and benzyl, and (vi) B is either R or COY wherein Y is selected from $-NHR^7$, $-OR^7$ and $-SR^7$ where $R^7$ is a hydrocarbyl group is provided. The compounds are efficient asymmetric hydrogenating agents for prochiral carbonyl containing compounds when used in single enantiomer form.

15 Claims, No Drawings

CHIRAL ORGANOIRON COMPLEXES AND USE FOR ASSYMETRIC REDUCTION

The present invention relates to new chiral organometallic complexes for the asymmetric hydrogenation of prochiral carbonyl containing compounds to single enantiomers of corresponding hydroxyl containing compounds. Such hydroxyl compounds are used industrially in the manufacture of pharmaceuticals, agrochemicals and other fine chemicals.

The enzymatic conversion of prochiral ketones to chiral alcohols can be mediated by the nicotinamide coezymes NADH and NADPH. In most cases this conversion is not only highly stereoselective to a preferred enantiomer of the chiral alcohol but is also catalytic with respect to the coenzyme. As a consequence, there has been much interest in the prior art in mimicing this conversion by using model analogues. For example in Lecture Notes in Bio-Inorganic Chemistry Vol. 1 (1986) Springer Verlag the use of various chiral 1,4-dihydroxy pyridines as model analogues is described. However such processes suffer from the disadvantage that they have only been proven stoichiometrically and attempts to render them catalytic have not met with success. The few catalytic reactions which have been reported are confined to non-chiral model analogues and even these are very slow and inefficient (see for example Tetrahedron Letters 1978 4815, Nouv J Chim 1984 8 719 and 1985 9 389).

A new family of model analogues based on N-substituted -1,4-dihydroxy pyridines modified with a chiral organometallic auxiliary has now been discovered whose members are efficient agents for the asymmetric hydrogenation of prochiral carbonyl containing compounds such as ketones, acyl or aroyl formates.

According to the present invention there is provided compounds having the general formula (I).

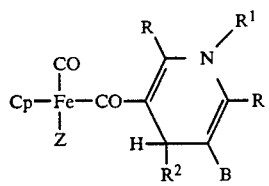

wherein
(i) Cp is either a cyclopentadienyl ligand having the formula $C_5(R^3)_5$ where the $R^3$ groups are independently hydrogen, methyl or ethyl or an indenyl ligand;
(ii) Z is a ligand having the formula $X(R^4)_2(Y)$ wherein X is selected from phosphorus, arsenic or antimony; the $R^4$ groups are independently aryl or aroxy and Y is selected from $-R^5$ $-NHR^5$ and $-OR^5$ wherein $R^5$ is a hydrocarbyl group;
(iii) the R groups are independently hydrogen, halogen or $C_1$ to $C_4$ alkyl;
(iv) $R^1$ is selected from hydrogen, $C_1$ to $C_6$ alkyl, benzyl and $-CO_2R^6$ where $R^6$ is $C_1$ to $C_6$ alkyl;
(v) $R^2$ is selected from hydrogen, $C_1$ to $C_{10}$ alkyl, phenyl and benzyl, and
(vi) B is either R or COY wherein Y is selected from $-NHR^7$, $-OR^7$ and $-SR^7$ where $R^7$ is a hydrocarbyl group.

Compounds of formula (I) are chiral and for the purposes of asymmetric hydrogenation it is preferred that only one of the two possible enantiomers is employed. Thus in an embodiment of the present invention there is provided a single enantiomer of a compound of general formula (I) in substantially optically pure form. By the term substantially optically pure form, it is meant that one of the two possible enantiomers of the given compound comprises at least 95 mole % of the total sample.

Considering the compounds of general formula (I) further, it is preferred that the Cp ligand is selected from cyclopentadienyl ($C_5H_5$), pentamethylcyclopentadienyl ($C_5(CH_3)_5$), monomethylcyclopentadienyl ($C_5H_4(CH_3)$) or indenyl. The cyclopentadienyl is bonded eta-5, i.e. face on to the iron atom. The ligand Z is suitably one where X is phosphorus and the $R^4$ groups are selected from phenyl, phenoxy, $C_1$ to $C_6$ alkyl substituted phenyl and $C_1$ to $C_6$ alkyl substituted phenoxy. It is preferred that both R groups are phenyl or independently $C_1$ to $C_4$ alkyl substituted phenyl.

The remaining group Y attached to Z preferably has either of the formulae $-R^5$ and $-OR^5$ where $R^5$ is a hydrocarbyl group. One preferred class of $R^5$ groups are $C_1$ to $C_{10}$ alkyl or alkoxy groups. Another class is provided by phenyl, phenoxy, $C_1$ to $C_6$ alkyl substituted phenyl or $C_1$ to $C_6$ alkyl substituted phenoxy groups. Most preferred examples of Z are triphenylphosphine, diphenylcyclohexylphosphine, triphenylphosphite and diphenylcyclohexylphosphite.

In a particularily preferred sub-class of compounds of formula (1), the ligand Z is itself chiral. The most suitable way of introducing chirality into such ligands is to make the Y group chiral. Preferred chiral Y groups are those wherein the $R^5$ contains a chiral centre and it is particularily preferred that Y is $-OR^5$ and that $-OR^5$ is derived from a corresponding chiral alcohol of formula $HOR^5$. Preferred chiral alcohols from which the $-OR^5$ can be derived include the enantiomers of naturally occuring chiral alcohols e.g. menthol, borneol, and the like.

When the ligand Z is chiral it is preferred to use only one of the two possible enantiomers in the synthesis of the corresponding compound of formula (1).

As regards the other groups attached to the compound, the R groups on the heterocyclic moiety are preferably either hydrogen or methyl. Most preferably all the R groups are hydrogen. The $R^2$ group is preferably selected from hydrogen, methyl, ethyl, phenyl and benzyl. $R^1$ is preferably selected from hydrogen, $C_1$ to $C_4$ alkyl, benzyl, and $-CO_2R^6$ where $R^6$ is $C_1$ to $C_4$ alkyl or phenyl.

Turning to the hydrocarbyl group $R^7$ which may form part of the group B, this can be in principle any group but is preferably one having one or more chiral centres. Suitable groups include $C_1$ to $C_{10}$ alkyl or hydroxyalkyl groups or derivatives thereof substituted with aryl groups, e.g. phenyl, $-OH$, halogen, $-CN$, $-OR$ and the like. A preferred class of $R^7$ groups are those where the chiral centre is adjacent to the nitrogen, oxygen or sulphur atom in Y. One class of such $R^7$ groups have the formula $-C(Ph)(R^8)_2$ where the $R^8$ groups are selected from hydrogen, $-OH$, $-Cl$, $-Br$, $-CN$, $-OR$ and $C_1$ to $C_6$ alkyl or hydroxyalkyl with the proviso that they are non-identical.

Other preferred classes of such $R^7$ groups are those chosen so that COY constitutes a beta-hydroxy-carboxamide group. Examples of suitable $R^7$ groups include $-(C(R^9)HCH(R^{10})(OH))$ where $R^9$ is $C_1$ to $C_6$ alkyl, phenyl or $CO_2R^{11}$ where $R^{11}$ is $C_1$ to $C_6$ alkyl and $R^{10}$ is hydrogen, $C_1$ to $C_6$ alkyl or phenyl.

A compound of formula (I) in which $R^1$ is $C_1$ to $C_6$ alkyl or benzyl and B is R is suitably prepared by reducing the corresponding compounds of formula (II).

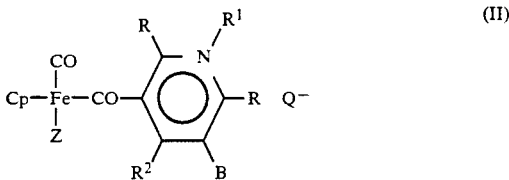
(II)

where $Q^-$ is an anion e.g. halide. A very suitable class of reducing agents for compounds of formula (II) is the alkali metal dithionites of formula $M_2S_2O_4$ where M is preferably either sodium or potassium. The reduction is suitably carried out at or below room temperature under an inert atmosphere e.g. argon, nitrogen etc., in a two phase system using aqueous dithionite and solvent such as dichloromethane and/or methanol.

An alternative method of preparing a compound of formula (I) comprises treating a corresponding compound of formula:

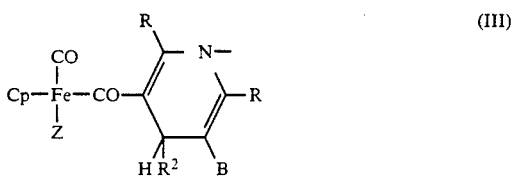
(III)

with an electrophile. Typical electrophiles include alcohols, e.g. methanol, for generating species in which $R^1=H$, haloformate esters of formula $ClCO_2R^6$ or $BrCO_2R^6$ ($R^1=CO_2R^6$) and sulphates of formula $(R^1O)_2SO_2$ or halides of formula $R^1Br$ or $R^1I$ ($R^1=C_1$ to $C_6$ alkyl or benzyl). Such reactions are preferably carried out in an appropriate solvent, e.g. THF, at or below room temperature under an inert atmosphere.

Compounds of formula (II) are suitably prepared by quaternisation of compounds of formula:

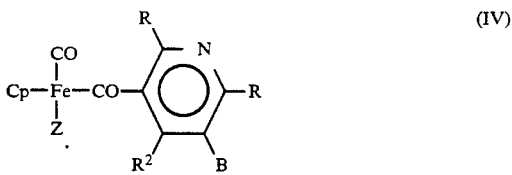
(IV)

with a quaternising agent of formula $R^1Q$. Suitable quaternising agents include iodides or bromides of formula $R^1Q$ or $R^1$ esters of sulphonic acids.

Compounds of formula (III), where $R^2$ is other than hydrogen, are suitably prepared by para-selective alkylation of compounds of formula (V):

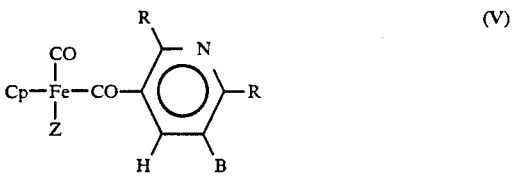
(V)

Typical alkylating/arylating agents are those having the formula $R^2_nB$ where B is a Group IA, IIA or IIIA metal and n is an integer corresponding to the oxidation state of the particular metal used. Examples include methyl lithium, n-butyl lithium, phenyl lithium trimethyl aluminium and the like.

Compounds of formula (IV) and (V) can be prepared in two steps from a salt of the anion $CpFe(CO)_2^-$.

In a first step the salt is treated with a pyridine derivative either of formula:

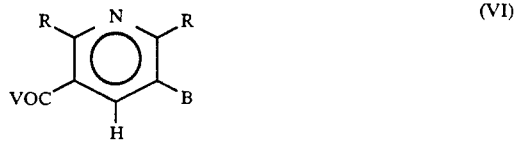
(VI)

or

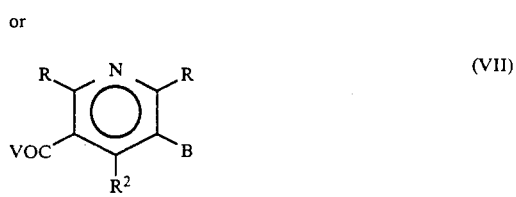
(VII)

where V is either Cl or Br. The product of the first step, which either has the formula:

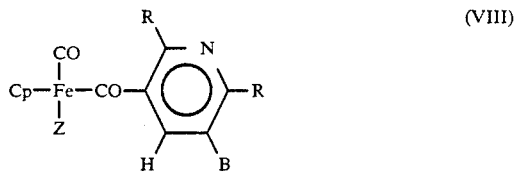
(VIII)

or

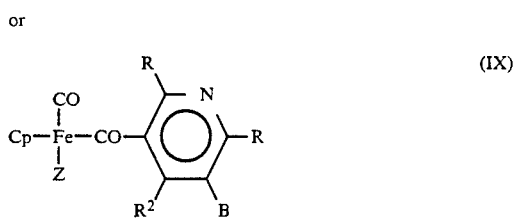
(IX)

is thereafter photolysed in the presence of the ligand Z to produce the desired product. Photolysis can be typically effected using the ultra-violet light from a medium pressure mercury arc lamp.

Alternatively, compounds of formula (IV) and (V) can be prepared by reacting the anion of formula $CpFe(CO)Z^-$ with compounds of formula (VI) or (VIII). The anion $CpFe(CO)Z^-$ can be prepared from the corresponding carbonyl hydride $CpFe(CO)H^-$ and the ligand Z.

The compounds of general formula (I) in wich B is COY are suitably prepared by photolysing the corresponding precursor.

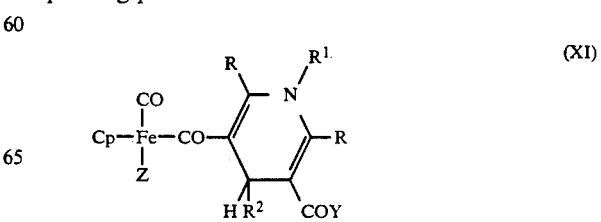
(XI)

in the presence of the ligand Z. Typically this photolysis is carried out by ultra violet irradiation in an inert dry solvent. Such precursors can themselves be prepared by quaternisation and subsequent reduction of the corresponding pyridine precursor.

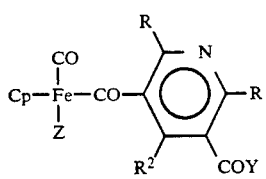
(XII)

Typical quaternising agents include the iodide or bromide derivatives of formula $R^1I$ or $R^1Br$ whilst reduction of the quaternished material can be effected with for example an alkali metal dithionite.

The pyridine precursor (XII) is suitably prepared from the anion $[CpFe(CO)_2]^-$ by (a) treatment with a substituted pyridine of formula

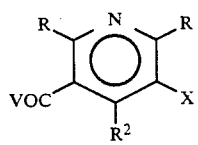
(XIII)

where the X groups are independently halogen (e.g. Cl, Br or I) to yield the intermediate

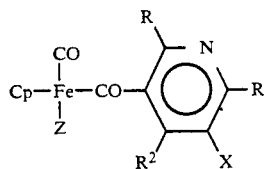
(XIV)

and (b) thereafter carbonylating the intermediate (XIV) with carbon monoxide in the presence of either an amine of formula $R^7NH_2$ or an alcohol of formula $R^7OH$ or a thiol of formula $R^7SH$ in the presence of a palladium catalyst. Both steps are suitably carried out in a dry solvent (e.g. THF). Step (a) is suitably carried out below room temperature whilst step (b) is carried out at elevated temperature under an overpressure of carbon monoxide.

The compound of formula (I) where B is COY can also be prepared from the anion of formula $CpFe(CO)Z^-$ by an analogous series of reaction although in this case a photolysis step is not required. It is possible to prepare the anion from the corresponding hydride CpFe(CO)ZH using standard techniques.

It has been discovered that compounds of formula (I) are efficient agents for the asymmetric reduction of prochiral carbonyl containing compounds such as ketones, acyl or aroyl formates.

According to an embodiment of the present invention there is provided a process for preparing a single enantiomer of a hydroxyl containing compound which is chiral at the carbon atom bonded to the hydroxyl group which process comprises reducing a carbonyl containing compound which is prochiral at the carbonyl group with a single enantiomer of a chiral iron compound having the formula (I) above at a temperature below 25° C. under conditions in which the chiral iron compound is oxidised.

In a first embodiment of the process defined above, the prochiral carbonyl containing compound is treated with the chiral iron compound in a single liquid phase in the presence of a Lewis acid. Preferred Lewis acids are magnesium or zinc salts e.g. magnesium perchlorate. The process is suitably carried out in a nitrile solvent, preferably at $C_1$ to $C_6$ alkyl nitrile or benzonitrile solvent. Most preferred is acetonitrile. Other polar solvents, e.g. dichloromethane, THF, etc., can also be used.

The reaction is suitably carried out under an inert atmosphere e.g. argon, nitrogen and the like at a temperature below 25° C. preferably in the range 0° C. to 25° C. It is preferred that all the components used are substantially dry.

Whilst not wishing to be bound by any theory, it is believed that during the treatment step the prochiral carbonyl containing compound is reduced by the chiral iron compound which in turn is oxidised stoichiometrically to a single enantiomer of a chiral compound having the general formula:

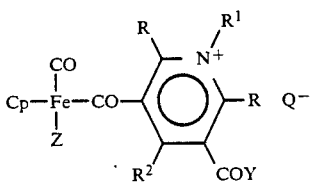
(II)

where $Q^-$ is an anion.

The chiral compound of formula (II) can be separated from the product mixture and reconverted into a compound of formula (I) by reduction using a reducing agent such as an alkali metal dithionite salt e.g. the potassium or sodium salt. The process of the first embodiment can therefore be operated cyclically so that only the Lewis acid and the dithionite, which are readily available cheap materials, are consumed.

In a second embodiment of the present invention, the prochiral carbonyl containing compound is treated with the chiral iron compound of formula (I) using a two phase system comprising an aqueous phase and an immiscible organic phase. In this system asymmetric hydrogenation of the prochiral carbonyl containing compound takes place in the organic phase and reduction of the chiral iron compound of formula (II) takes place in the aqueous phase.

As regards the immiscible organic phase this is preferably either a halogenated organic compound, such a dichloromethane, chloroform, carbon tetrachloride and the like or a nitrile such as acetonitrile.

The aqueous phased used is a solution of an appropriate reducing agent such as an alkali metal dithionate. The aqueous phase is suitably buffered to a pH e.g. in the range 6 to 7 (25° C.).

The organic phase may optionally contain magnesium or zinc as described above. However this is not a prerequisite for the process and it has been found that the hydrogenation will take place in the organic phase even when no magnesium or zinc is present.

The process of the second embodiment is suitably carried out at a temperature below 25° C. preferably between 0° C. and 25° C. under an inert atmosphere.

Whilst the process of the embodiment of the present invention can be applied to any prochiral carbonyl containing compounds e.g. ketones, acyl or aroyl formates, it is particularly suited to the reduction of acyl or aroyl formates according to the equation:

$$R^{12}COCO_2R^{13} + 2H \rightarrow R^{12}\text{·}CH(OH)CO_2R^{13}$$

wherein $R^{12}$ is $C_1$ to $C_{10}$ alkyl or phenyl and $R^{13}$ is $C_1$ to $C_{10}$ alkyl, phenyl or hydrogen. In such a process chirality is created at the carbon asterisked. Preferred $R^{12}$ and $R^{13}$ groups are $C_1$ to $C_4$ alkyl or phenyl.

The following Examples now illustrate the invention.

EXPERIMENTAL

All reactions and purifications were performed under nitrogen atmosphere using standard vacuum line and Schlenk tube techniques. Removal of all solvent was carried out under reduced pressure. (THF) was dried over sodium benzophenone ketyl and distilled. Dichloromethane was distilled from calcium hydride. Hexane refers to the fraction boiling in the range 67°-70° C. Methyllithium (1.4M in diethyl ether; low halide content) and n-butyllithium (1.6M in hexane) was used as supplied by Aldrich. Phenyllithium (0.35M in diethyl ether) was prepared from lithium wire and bromobenzene according to a standard literature method. I.r. spectra were recorded in dichloromethane on a Perkin-Elmer 297 instrument. Proton n.m.r. spectra were recorded on a Bruker WH 300 spectrophotometer at 300.13 MHz and referenced to residual protio-solvent, with chemical shifts being reported as delta ppm from $(CH_3)_4Si$. Carbon-13 n.m.r. spectra were recorded on a Bruker AM 250 spectrometer at 62.90 MHz using $CDCl_3$ as solvent and internal standard and are reported as delta ppm from $(CH_3)_4Si$. Phosphorus-31 n.m.r. spectra were recorded on a Bruker AM 250 spectrometer at 101.26 MHz using $CDCl_3$ as solvent and are reported as delta ppm from an external reference of triethylphosphate in $D_2O$. Mass spectra were recorded on a V.G. micromass ZAB 2F instrument using EI and FD techniques.

EXAMPLE 1

Preparation of [($n^5$-$C_5H_5$)Fe(CO)$_2$CO-3-pyridine] (VIII; R=H)

Freshly distilled nicotinyl chloride (21.27 g, 150.2 mmol) prepared according to literature methods, was added over 20 min as a solution in THF (50 ml) to a stirred solution of [($n^5$-$C_5H_5$)Fe(CO)$_2$]$^-$Na$^+$ (prepared from 24.00 g, 67.8 mmol of cyclopentadienyldicarbonyliron dimer) in THF (400 ml) at $-78°$ C. The mixture was stirred for 2 h at $-78°$ C. and then allowed to warm to ambient temperature and stirred overnight. The solvent was removed, dichloromethane (500 ml) added and the resulting solution filtered through Celite. The crude product was concentrated and chromatographed over alumina (Grade I); purple/red cyclopentadienyldicabonyliron dimer eluted first (1:1 hexane diethyl ether) followed by the yellow desired product (ethyl acetate). Removal of solvent gave the desired product (27.47 g, 72%) as a yellow crystalline solid. An analytically pure sample was obtained by recrystallisation from dichloromethane/cyclohexane (Found: C 55.4; H 3.1; N 4.8. $C_{13}H_9FeNO_3$ requires C 55.16; H 3.20; No.95%); v. max. 2100vs (C=O), 1965vs (C=O), 1600s cm$^{-1}$ (C=O), $^1$H n.m.r. ($C_6D_6$) 9.09 (1H, bs, 2-H), 8.49 (1H, bd, $^3J_{HH}$ 3.7 Hz, 6-H), 7.54 (1H, dt, $^3J_{HH}$ 7.9 Hz, $^4J_{HH}$ 2.0 Hz, 4-H), 6.70 (1H, dd, $^3J_{HH}$ 7.9, 4.7 Hz, 5-H), 4.04 (5H, s, $C_5H_5$); $^{13}C(^1H)$ n.m.r. 213.30 (s, C=O), 150.50 (s, 6-C), 147.29 (s, 2-C), 145.07 (s, 3-C), 132.31 (s, 4-C), 123.31 (s, 5-C), 86.23 (s, $C_5H_5$); m/z 283 (M$^+$), 255 (M$^+$-28).

EXAMPLE 2

Preparation of [($n^5$-$C_5H_5$)Fe(CO)(PPh$_3$)CO-3-pyridine](V: R=H, Z=PPh$_3$)

A suspension of finely ground product from Example 1 (2.66 g, 9.4 mmol) in a solution of triphenylphosphine (3.70 g, 14.1 mmol) in cyclohexane (140 ml) was irradiated internally in a quartz immersion apparatus using a Hanovia 125-W medium pressure mercury arc lamp. The reaction was monitored by ir (disappearance of carbonyl stretches at 2100 and 1965 cm$^{-1}$) and irradiation stopped after 72 h. The product, an orange precipitate which coated the walls of the reaction vessel, was separated by filtration, washed with cyclohexane, then dissolved in $CH_2Cl_2$ and filtered through alumina (Grade V). The solvent was removed and the residue crystallised from hexane/$CH_2Cl_2$ to give the desired product (3.94 g, 81%) as a orange crystalline solid (Found: C 69.4; H 4.8; N 2.7; P 5.8. $C_{30}H_{24}FeNO_2P$ requires C 69.65; H 4.68; N 2.71; P 5.99%); v. max. 1940vs (C=O), 1580s cm$^{-1}$ (C=O); $^1$H n.m.r. (CDCl$_3$) 8.46 (1H, dd, $^3J_{HH}$ 4.7 Hz, $^4J_{HH}$ 1.6 Hz, 6-H), 8.20 (1H, d, $^4J_{HH}$ 1.5 Hz, 2-H), 7.50–7.28 (15H, m, Ph), 7.23 (1H, dt, $^3J_{HH}$ 7.9 Hz, $^4J_{HH}$ 1.9 Hz, 4-H), 7.12 (1H, dd, $^3J_{HH}$ 7.9, 4.8 Hz, 5-H), 4.59 (5H, d, $^3J_{PH}$ 1.3 Hz, $C_5H_5$); $^{13}C(^1H)$ n.m.r. 220.43 (d, $^2J_{PC}$ 31.6 Hz, C=O), 149.46 (s, 6-C), 147.30 (s,2-C), 146.61 (s, C-3), 135.85 (d, $^1J_{PC}$ 43.6 Hz, Ph C$_{ipso}$), 133.31 (d, $^2J_{PC}$ 9.8 Hz, Ph C$_{ortho}$), 132.64 (s, 4-C), 129.87 (s, Ph C$_{para}$), 128.13 (d, $^3J_{PC}$ 9.4 Hz, Ph C$_{meta}$), 122.43 (s, 5-C), 85.39 (s, $C_5H_5$); $^{31}P(^1H)$ n.m.r. 70.66; m/z 517 (M$^+$).

EXAMPLE 3

General Procedure for the Sequential Reaction of the product of Example 2 with Nucleophiles and Electrophiles Alkyl or aryllithium (0.9 mmol; 5.8 mmol in the case of methyllithium) was added to the product of Example 2 (300 mg, 0.58 mmol) in THF (50 ml) at $-78°$ C. to give a deep red solution. The mixture was stirred at $-78°$ C. for 1 h (where methyllithium was used the mixture was warmed to $-40°$ C. and stirred for a further 2 h then recooled to $-78°$ C.). Methanol (1 ml), chloroformate (3.2 mmol; 6.4 mmol when methyllithium was used), or dimethyl sulphate (0.25 ml, 2.64 mmol; 0.75 ml, 7.92 mmol when methyllithium was used) was then added dropwise to give an orange solution. For the methanol and chloroformate reactions the mixture was stirred at $-78°$ C. for a further 0.5 h, warmed to room temperature and the solvent removed. For dimethylsulphate the mixture was allowed to warm to ambient over 2 h, stirred for 1 h, and saturated NaHCO$_3$ (20 ml) added. The resulting mixture was then stirred for 2 h, the organic layer separated, the aqueous layer washed with dichloromethane (2×30 ml) and the combined organics concentrated. The orange oil which was obtained from each reaction was extracted with dichloromethane (3×10 ml) and filtered through alumina (Grade V). The crude product complexes were analysed by $^1$H n.m.r. (300 MHz) spectroscopy. The product complexes were purified by chromatography on alumina (Grade V, Products D-F) eluted with 1:1 dichloromethane diethyl ether, (G-J) and (K,L) eluted with diethyl ether, any unreacted complex eluted with dichloromethane), and crystallised from dichloromethane-hexane. The products produced are shown in the Table.

TABLE

Product Produced in Example 3 Reactions

| Sample | Nucleophile/Electrophile used | Reactant | Product |
|---|---|---|---|
| | | Compound (V) | Compound (III) |
| A | MeLi | Z=PPh$_3$, R=H | as for (V), R$^2$=Me |
| B | PhLi | Z=PPh$_3$, R=H | as for (V), R$^2$=Ph |
| C | $^n$BuLi | Z=PPh$_3$, R=H | as for (V), R$^2$=$^n$Bu |
| | | Compound (III) | Compound (I) |
| D | Methanol | Product A | as for (III), R$^1$=H |
| E | Methanol | Product B | as for (III), R$^1$=H |
| F | Methanol | Product C | as for (III), R$^1$=H |
| G | ClCO$_2$Me | Product A | as for (III), R$^1$=CO$_2$Me |
| H | ClCO$_2$Me | Product B | as for (III), R$^1$=CO$_2$Me |
| I | ClCO$_2$Me | Product C | as for (III), R$^1$=CO$_2$Me |
| J | ClCO$_2$Ph | Product A | as for (III), R$^1$=CO$_2$Ph |
| K | (MeO)$_2$SO$_2$ | Product A | as for (III), R$^1$=Me |
| L | (MeO)$_2$SO$_2$ | Product B | as for (III), R$^1$=Me |

EXAMPLE 4

Preparation of
(RS)[n$^5$-C$_5$H$_5$)Fe(CO)PPh$_3$)CO-3-(N-methyl-1,4-dihydropyridine)]

Methyl iodide (4 ml) was added to an orange solution of the product of Example 2 (1.368 g, 2.65 mmol) in dichloromethane (60 ml). Stirring for 18 h at ambient temperature gave a red solution. Removal of solvent gave crude (RS)-[(n$^5$-C$_5$H$_5$)Fe(CO) (PPh$_3$)CO-3-(N-methylpyridine)]$^+$I$^-$ as an orange brown amorphous solid; v. max. 1920 vs (C O), 1560s cm$^{-1}$ (C=O); $^1$H n.m.r. (CD$_2$Cl$_2$) 9.27 (1H, d, $^3$J$_{HH}$ 5.9 Hz, 6-H), 8.01 (1H, d, $^3$J$_{HH}$ 8.0 Hz, 4-H), 7.90 (1H, dd, $^3$J$_{HH}$ 7.9, 5.9 Hz, 5-H), 7.52–7.35 (15H, m, Ph), 7.25 (1H, s, 2-H), 4.74 (5H, d, $^3$J$_{PH}$ 1.0 Hz, C$_5$H$_5$), 4.40 (3H, s, CH$_3$); m/z 532 (M$^+$ of cation).

The pyridinium complex was dissolved in a mixture of methanol (20 ml) and dichloromethane (80 ml) and added to a solution of sodium dithionite (85%; 5.00 g, 24.41 mmol) and sodium hydrogen carbonate (3.00 g, 35.71 mmol) in distilled water (60 ml). The resulting two-phase mixture was stirred vigorously for 16 h in the dark. The organic layer was separated, the aqueous layer was washed twice with dichloromethane (2×30 ml) and the combined organics concentrated. Chromatography over alumina (Grade V) gave, on elution with dichloromethane, the desired product (1.204 g, 85%) as an orange solid. Red needles were obtained, on crystallisation from ethanol-hexane, which contained 1 equivalent of ethanol (Found C 68.7; H 5.75; N 2.2; P 5.3. C$_{31}$H$_{28}$FeNO$_2$P+CH$_3$CH$_2$OH requires C 68.40; H 5.91; N 2.42; P 5.35%). Crystallisation from dichloromethane-n-heptane gave the pure 1,4-dihydropyridine as an orange solid (Found C 69.84; H 5.59; N 2.81. C$_{31}$H$_{28}$FeNO$_2$P requires C 69.81; H 5.29; H 2.63%); H 2.63%); $\nu$max. 1905$^{vs}$ (C O), 1740m (C=C), 1600s cm$^{-1}$ (C=O); $^1$H n.m.r. 7.58–7.30 (15H, m, Ph), 6.98 (1H, d, $^4$J$_{HH}$ 1.4 Hz, 2-H), 5.67 (1H, dd, $^3$J$_{HH}$ 7.9 Hz, $^4$J$_{HH}$ 1.5 Hz, 6-H), 4.65 (1H, dt, $^3$J$_{HH}$ 7.9, 4.2 Hz, 5-H), 4.442 (5H, d, $^3$J$_{PH}$ 1.2 Hz, C$_5$H$_5$), 3.05 (3H, s, CH$_3$), 2.92 (1H, bd part of AB system, $^2$J$_{HH}$ 19.2 Hz, pro-R 4-H), 2.35 (1H, bd part of AB system, 2J$_{HH}$ 19.2 Hz, pro-S 4-H); $^{13}$C($^1$H) n.m.r. 222.44 (d, $^2$J$_{PC}$ 36.3 Hz, C O), 147.31 (s, 2-C), 137.11 (d, $^1$J$_{PC}$ 42.1 Hz, Ph C$_{ipso}$), 133.46 (d, $^2$J$_{PC}$ 9.3 Hz, Ph C$_{ortho}$), 129.43 (s, 6-C), 129.39 (s, Ph C$_{para}$), 127.88 (d, $^3$J$_{PC}$ 9.5 Hz, Ph C$_{meta}$), 124.84 (s, 3-C), 105.23 (s, 5-C), 85.17 (s, C$_5$H$_5$), 41.07 (s, CH$_3$), 24.06 (s, 4-C), $^{31}$P($^1$H) n.m.r. 73.38; m/z 533 (M$^+$).

EXAMPLE 5

Preparation of
(R)-(+))-[(n$^5$-C$_5$H$_5$)Fe(CO)(PPh$_2$(0-(L)-menthyl) CO-3-pyridine] (V: R=H, Z=PPh$_2$(O-(L)-menthyl))

A solution of the product of Example 1 (3.6 g, 12.7 mmol) and diphenylphosphinic acid (L)-menthyl ester (6.0 g, 16 mmol, prepared according to literature methods) in dichloromethane (70 ml) was irradiated internally using a Hanovia 125-W medium pressure mercury arc lamp. The reaction was monitored by ir (see Example 2) and the irradiation was stopped after 5 hours. The reaction mixture was then concentrated and chromatographed over alumina (Grade V) and the unreacted phosphinic ester was eluted with hexane. On elution with diethyl ether, a 1:1 mixture of the (R)- and (S)-diastereoisomers of the desired product were obtained (4.12 g, 44%). Unreacted product of Example 1 (1.58 g, 44%) was thereafter eluted with dichloromethane.

The mixture of diastereoisomers was dissolved in dichloromethane/hexane (approx 1:5 by weight) and the (R)-(+)-diastereoisomer was allowed to crystallise at −20° C. (0.86 g, 11% d.e. better than 150:1 by $^{31}$p NMR). Found: [alpha]$_{546}^{27}$+204.5, [alpha]$_{578}^{27}$+154.9, [alpha]$_{589}^{27}$+142.5 (c 0.07, C$_6$H$_6$); analysis C68.4, H 6.5, N 2.31, P 5.19.

EXAMPLE 6

Preparation of
(R)-(+)-[(n$^5$-C$_5$H$_5$)Fe(CO)(PPh$_2$(0-(L)-menthyl) CO-3-(N-methylpyridinium iodide)](II: R$^2$=H, R=H, R$^1$=CH$_3$, Q=I and Z=PPh$_2$(0-(L)-menthyl))

0.632 g (0.106 mmol) of the product of Example 5 was dissolved in 15 ml of dichloromethane. Iodomethane (2 ml) was then added and the mixture stirred for 18 hours at room temperature. Removal of solvent and drying gave the desired product (0.781 g 100%). Found: [alpha]$_{546}^{26}$+353.9, [alpha]$_{578}^{26}$+250.9, [alpha]$_{589}^{26}$+233.0 (C0.05 acetone); analysis C 56.75, H 5.71, N 1.77.

EXAMPLE 7

Preparation of
(R)-(−)-[(n$^5$-C$_5$H$_5$)Fe(CO)(PPh$_2$(0-(L)-menthyl)-3-(N-methyl-1,4-dihydropyridine)] (I: R$^2$=H, R=H, R$^1$=CH$_3$ and Z=PPh$_2$(O-(L)-menthyl)

A solution of the product of Example 6 (0.721 g, 1.03 mmol) in dichloromethane (30 ml) was added to a solution of sodium dithionite (85%, 2.5 g 12.2 mmol) in 0.25M phosphate buffer (30 ml, pH=7). The mixture was then stirred for 36 hours in the dark after which the organic layer was separated. The aqueous layer was washed with dichloromethane (2×30 ml) and the organics were then combined and concentrated. A solution of the crude product in dichloromethane was filtered through a short plug of Grade V alumina to yield the desired product (0.461 g, 73%). Found [alpha]$_{546}^{23}$−129.9, [alpha]$_{578}^{23}$−107.3, [alpha]$_{589}^{23}$−103.9 (c 0.12 acetone).

EXAMPLE 8 a. Asymmetric Reduction of Ethyl Benzoylformate by Product of Example 3

To a solution of ethyl benzoylformate (0.0289 g, 0.162 mmol) in dry acetonitrile (3 ml) was added the product of Example 3 (0.0902 g, 0.169 mmol), followed by magnesium (II) perchlorate (0.0323 g, 0.145 mmol), and 4 A molecular sieve. The solution was stirred under nitrogen at ambient in the dark and the reaction followed by gas chromatography. Ethyl benzoylformate eluted first-followed by ethyl mandelate, as determined by comparison with authentic samples. After 21 h the yield of ethyl mandelate did not rise above 45%. The solvent was carefully removed under vacuum. The residue was extracted with diethyl ether (3×3 ml). Radial chromatography (1 mm thick silica gel plate) gave unreacted ethyl benzoylformate (on elution with 20% diethyl ether/hexane) followed by ethyl mandelate (on elution with 40% diethyl ether/hexane) (8.7 mg, 29%) which was pure by gas chromatography; $^1$H n.m.r. 7.47–7.30 (5H, m, Ph), 5.17 (1H, s, CHOH), 4.32–4.12 (2H, m, OCH$_2$CH$_3$), 3.63 (1H, bs, CHOH), 1.23 (3H, t, $^3J_{HH}$ 7.1 Hz, OCH$_2$CH$_3$): Identical to that of an authentic sample.

In a similar reaction conducted in the presence of 1 equivalent of zinc (II) bromide instead of magnesium (II) perchlorate, the yield of ethyl mandelate determined by gas chromatography was 35%.

b. Catalytic Reduction of Ethyl Benzoylformate Recycling of Complex

To a solution of ethyl benzoylformate (0.1106 g, 0.621 mmol) and the product of Example 3 (0.0123 g, 0.019 mmol) in dichloromethane (2 ml) was added an aqueous solution of sodium dithionite (85%; 0.430 g, 2.10 mmol) in 0.25M aqueous phosphate buffer (pH 7, 2.5 ml). The mixture was stirred vigorously under nitrogen in the dark at ambient temperature. After 20 h the yield of ethyl mandelate (as determined by gas chromatography) was 75%, which corresponds to 25 catalytic cycles.

Removal of the aqueous layer followed by the addition of a fresh solution of sodium dithionite (85%; 0.450 g, 2.20 mmol) in 0.25M phosphate buffer (pH 7; 2.5 ml) increased the yield of ethyl mandelate to 90% after 23 h. The aqueous layer was replaced a second time by a fresh solution of sodium dithionite (85%; 0.397 g, 1.94 mmol) in 0.25M phosphate buffer (pH 7, 2.5 ml) and ethyl benzoylformate (0.0843 g, 0.474 mmol) was added. After a further 24 h the yield of ethyl mandelate was 85%, which corresponds to 63 catalytic cycles.

COMPARATIVE TEST

Attempted Reduction of Ethyl Benzoylformate by Sodium Dithionite

To a solution of ethyl benzoylformate (0.0627 g, 0.352 mmol) in dichloromethane (3 ml) was added an aqueous solution of sodium dithionite (0.346 g, 1.69 mmol) in 0.25M aqueous phosphate buffer (pH 7, 2 ml). The mixture was stirred vigorously under nitrogen at ambient temperature. Monitoring the reaction by gas chromatography indicated very slow reduction of ethyl benzoylformate to ethyl mandelate. After 96 h the yield of ethyl mandelate was 25%.

ASYMMETRIC REDUCTION OF ETHYL BENZOYLFORMATE

EXAMPLES 9–11

To a solution of ethyl benzoylformate (0.2 mmol) in 0.7 ml of dry acetonitrile was added the appropriate compound of formula (I) (0.205 mmol) and magnesium perchlorate (0.2 mmol). The mixture was stirred under nitrogen in the dark at 20° C. for 1.5–24 hours. The reaction mixture was then quenched with a drop of water and the solvent removed in vacuo. The crude solid was taken up in dichloromethane and loaded on a silica gel column. Elution with a 10% EtOAC/hexane mixture yielded pure ethyl mandetate. Treatment of the residue with sodium dithionate yielded the appropriate compound of formula (I) (90%) which could be purified by recrystallisation or column chromatography. The compounds of formula (I), together with the yields of ethyl mandelate are given in the Table.

TABLE 1

| Example | Compound of Formula (I) | Time (hours) | Configuration of ethyl mandelate produced | Chemical Yield (%) | Optical Yield[2] (%) |
|---|---|---|---|---|---|
| 9 | RR-(Ia) | 24 | R | 68 | 90 |
| 10 | SR-(Ia) | 24 | S | 75 | 78 |
| 11 | RRS-(Ib) | 1.5 | R | 75 | 78 |

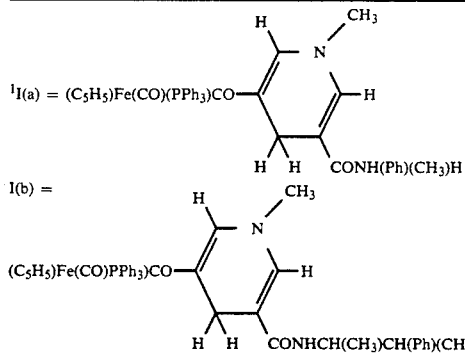

[1] I(a) = (C$_5$H$_5$)Fe(CO)(PPh$_3$)CO—

I(b) = (C$_5$H$_5$)Fe(CO)PPh$_3$)CO—

[2] Based on optical rotation of pure ethyl mandelate [alpha]$_D^{20}$ R enantiomer = −104° (c = 0.5, ethanol), [alpha]$_D^{20}$ for S enantiomer = +94° (c = 0.5, ethanol) and NMR analysis of the corresponding Mosher-ester derivatives.

EXAMPLES 12–17

The produce of Examples 1 to 3 was repeated using the appropriate compound of formula (I) as shown below. The following results were obtained.

TABLE 2

| Example | Compound of Formula (I) | Time (hours) | Configuration of ethyl mandelate produced | Chemical Yield (%) | Optical Yield (%) (See 2 above) |
|---|---|---|---|---|---|
| 12 | (RR)-(−)-(Ic) | 21 | R | 85 | 15(16) |
| 13 | (SS)-(+)-(Ic) | 8 | S | 64 | 16(18) |
| 14 | (SR)-(+)-(Id) | 12 | S | 84 | 97(99) |
| 15 | (RS)-(−)-(Id) | 8 | R | 82 | 97.5(99) |
| 16 | (RRS)-(−)-(Ie) | 1.5 | R | 75 | 97.8(98) |

TABLE 2-continued

| Example | Compound of Formula (I) | Time (hours) | Configuration of ethyl mandelate produced | Chemical Yield (%) | Optical Yield (%) (See 2 above) |
| --- | --- | --- | --- | --- | --- |
| 17 | (SSR)-(−)-(Ie) | 3 | S | 78 | 97(98) |

Structure of Compounds of formula (I)

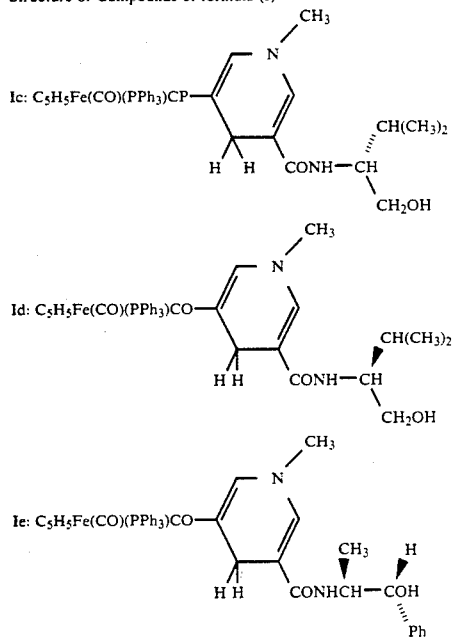

Ic: $C_5H_5Fe(CO)(PPh_3)CP$—

Id: $C_5H_5Fe(CO)(PPh_3)CO$—

Ie: $C_5H_5Fe(CO)(PPh_3)CO$—

EXAMPLE 18

Preparation of [(n$^5$-C$_5$H$_5$)Fe(CO)$_2$]-5-bromonicotinoyl

This compound which is an intermediate in preparing the compounds of formula (I) is prepared in three steps from methyl-3-bromonicotinic acid.

a. Preparation of 3-bromonicotinic acid

To a vigorously stirred solution of methyl-3-bromonicotinic acid (165 g, 0.764 mol) in a mixture of methanol (300 ml) and water (300 ml) was added potassium hydroxide until litmus paper indicated that the solution was basic (pH 10). The black solution was stirred at room temperature for 12 h and acidified with concentrated hydrochloric acid to a pH of approximately 2–3 resulting in a white precipitate. The slurry was then filtered, washed with water followed by ethanol and dried overnight on a vacuum pump to afford the corresponding acid (140.6 g, 91.5%) as a white solid. Analytically pure product was obtained as a white solid by crystallisation from acetic acid; m.p. 174°–175° C.;

b. Preparation of tert-butyric-3-bromonicotinic acid

To a slurry of the acid (140.6 g 0.699 mol) in dry benzene (1000 ml) was added triethylamine (140 ml, 1.00 mol) and the resulting mixture stirred at room temperature for 1 h. Pivoloyl chloride (100 ml, 4.75 mol) was then added to the inhomogeneous solution and stirred for 16 h. The resulting slurry was then filtered under vacuum, the filtrate washed with benzene (75 ml,×4) and the combined organics concentrated to afford the desired product (191 g, 95%) as a grey-white solid. Analytically pure product was obtained as a white solid by crystallisation from a mixture of dichloromethane/hexane (1:4); m.p. 172°–173° C.;

c. Preparation of [(n$^5$-C$_5$H$_5$)Fe(CO)$_2$]-5-bromonicotinoyl

To a stirred solution of cyclopentadienylirondicarbonyl anion (226 mmol) in tetrahydrofuran (1200 ml) at −78° C., was added a solution of tert-butyric-3-bromonicotinic acid (60.0 g, 210 mmol) in tetrahydrofuran (500 ml) over a period of 15 min. The reaction mixture was stirred for 3 h at −78° C. and the allowed to warm to room temperature and stirred overnight. The resulting slurry was filtered on Celite under vacuum, washed with dichloromethane (100 ml,×4), and the combined organics concentrated to give a brown solid which was crystallised at −20° C. from a mixture of dichloromethane/ethyl acetate (1:1) thus affording the desired product as yellow needles (68 g, 89%);

EXAMPLE 19

Preparation of the (RR)-(−)- and SR-(+)-diastereomers of [(n$^5$-C$_5$H$_5$)Fe(CO)(PPhz)]-1-methyl-5-(N-alpha methylbenzyl carbamoyl)-1,4-dihydronicotinoyl (Compound I (a) above)

These products were prepared in three steps form the product of Example 10.

a. Preparation of (R)-[(n$^5$-C$_5$H$_5$)Fe(CO)$_2$]-5-(N-alpha-methylbenzylcarbamoyl)nicotinoyl A Fisher-Porter bottle containing a mixture of the product of Example 10 (5.0 g, 13.8 mmol), palladium (II) chloride (98 mg, 0.04 mmol), triphenylphosphine (289 mg, 0.08 mmol) and (R)-(+)-alpha-methylbenzylamine (2.34 g, 27.6 mmol) in tetrahydrofuran (18 ml) was sealed under 5 atmospheres of CO and stirred at 100° C. for 7.5 h. Concentration of the black solution followed by column chromatography of the residue in dichloromethane on silica gel (elution with ethyl acetate/hexane, 1:1) afforded recovered starting material (300 mg, 6%) and further elution with ethyl acetate afforded the desired product (5.132 g, 86.5%) as yellow amorphous solid;

b. Preparation of (R)-[(n5-C5H5)Fe(CO)2]-1-methyl-5-(N-alpha-methylbenzyl carbamoyl)-1,4-dihydronicotinoyl To a solution of the product prepared above (1.65 g, 3.84 mmol) in dichloromethane (50 mL) was added iodomethane (10 mL) and the solution was gently refluxed for 20 h. Removal of solvent and drying gave the corresponding pyridinium salt (2.19 g, 100%) as a yellow amorphous solid. The pyridinium salt (2.19 g, 3.84 mmol) was dissolved in a mixture of methanol (20 ml) and dichloromethane (80 ml) and added to a solution of sodium dithionite (85%; 5 g, 28.74 mmol) and sodium hydrogen carbonate (3.0 g, 35.7 mmol) in distilled water (60 ml) and stirred vigorously for 6 h in the dark. The organic layer was separated, the aqueous layer washed with dichloromethane (2×30 ml), dried over magnesium sulphate and the combined organics concentrated affording the desired product (1.64 g 94%) as a yellow solid;

c. Preparation of (RR)-(−)-[(n5-C5H5)Fe(CO)(PPh3)]-1-methyl-5-(N-alpha-methyl benzylcarbomoyl)-1,4-dihydronicotinoyl and (SR)-(+)-[(n5-C5H5)Fe(CO)(PPh3)]-1-methyl-5-(N-alpha-methyl benzylcarbamoyl)-1,4-dihydronicotinoyl A solution of the product prepared above (3.70 g, 8.29 mmol) and triphenylphosphine (3.25 g, 12.43 mmol) in a mixture of cyclohexane (220 ml) and tetrahydrofuran (150 ml) was irradiated internally in a quartz immersion apparatus using a Hanovia 125-W medium pressure mercury arc lamp. The reaction was monitored by $^1H$ n.m.r. spectroscopy (appearance of C5H5 signal at 4.42 ppm) and irradiation stopped after 4 h. Concentration of the solvent followed by column chromatography of the crude oil on alumina (Grade V) (elution with diethyl ether/methanol 4%) afforded a 1:1 mixture of diastereomers (3.6 g 63%). Further careful column chromatography on alumina (Grade V) (elution with diethyl ether/methanol 4%) afforded the RR (800 mg, 15%), the SR form (600 mg, 11%) and a mixture of both (600 mg, 11%) as red crystalline solids.

Optical Data
RR diastereomer: [alpha]$_D^{22}$ = −547 (c 0.055 CH2Cl2)
SR diastereomer: [alpha]$_D^{22}$ = +141 (c 0.054 CH2Cl2).

EXAMPLE 20

Preparation of the (RS)-(−)- and SS-(+)-diastereomers of [(n5-C5H5)Fe (CO)(PPh3)]-1-methyl-5-(1-hydroxymethylisopropylcarbonyl)1,4-dihydronicotinyl These products were prepared in three steps from the product of Example 18.

a. Preparation of (S)-[(n5-C5H5)Fe(CO)2]-5-(1-hydroxymethylisopropylcarbamoyl) nicotinoyl A Fisher-Porter bottle containing the product of Exmaple 10 (5.0 g, 13.8 mmol), palladium (II) chloride (122 mg, 0.05 mmol), triphenylphosphine (302 mg, 0.10 mmol) and L-valinol (1.50 g, 14.56 mmol) in tetrahydrofurn (13 ml) was sealed under 5 atmospheres of CO and stirred at 100° C. for 2 h. Concentration of the black solution followed by column chromatography of the residue in dichloromethane on silica gel (elution with diethyl ether) afforded recovered starting material (1.5 g, 30%) and further elution with a mixture of diethyl ether/methanol (10%) afforded the desired product (3.4 g, 60%) as a pale yellow amorphous solid;

b. Preparation of (S)-[(n5-C5H5)Fe(CO)2]-1-methyl-5-(1-hydroxy methylisopropylcarbamoyl)-1,4-dihydronicotinoyl To a solution of the product prepared above (5.62 g, 13.6 mmol) in dichloromethane (100 mL) was added iodomethane (20 mL) and the solution was gently refluxed for 24 h. Removal of solvent and drying gave the corresponding pyridinium salt (7.54 g, 100%) as a yellow amorphous solid.

The pyridinium salt (7.54 g, 13.6 mmol) was dissolved in a mixture of methanol (20 ml) and dichloromethane (100 ml) and added to a solution of sodium dithionite (85%; 7.5 g, 43.10 mmol) and sodium hydrogen carbonate (5.0 g, 59.50 mmol) in distilled water (80 ml) and stirred vigorously for 2 h in the dark. The organic layer was separated, the aqueous layer washed with dichloromethane (2×30 ml), dried over magnesium sulphate and the combined organics concentrated. Drying under vacuum the desired product (5.4 g, 94%) as a yellow amorphous solid.

c. Preparation of (RS)-(−)-[(n5-C5H5)Fe(CO)(PPh3)]-1-methyl-5-(1-hydroxymethyl isopropylcarbamoyl)-1,4-dihydronicotinoyl and (SS)-(+)-[(n5C5H5)Fe(CO)(PPh3)]-1-methyl-5-(1-hydroxymethyl isopylcarbamoyl)-1,4-dihydronicotinoyl A solution of the product prepared above (5.4 g, 12.62 mmol) and triphenylphosphine (4.95 g, 16.92 mmol) in a mixture of cyclohexane (270 ml) and tetrahydrofuran (250 ml) was irradiated internally in a quartz immersion apparatus using a Hanovia 125-W medium pressure mercury arc lamp. The reaction was monitored by $^1H$ n.m.r. spectroscopy (appearance of C5H5 signal at 4.42 ppm) and irradiation stopped after 7.5 h. Concentration of the solvent followed by column chromatography of the crude oil on alumina (Grade V) (elution with diethyl ether/methanol 4%) afforded a 1:1 mixture of the desired diastereomers (4.1 g, 49%). Further careful column chromatography on alumina (Grade V) (elution with diethyl ether/methanol 4%) afforded the RS form (1.4 g, 17%), the SS form (1.1 g, 13%) and a mixture of both (1.5 g 18%).

Optical Data
RS diastereomer: [alpha]$_D^{22}$ = −394 (c 0.069 CH2Cl2)
SR diastereomer: [alpha]$_D^{22}$ = +394 (c 0.055 CH2Cl2).

I claim:
1. Compounds having the formula (I)

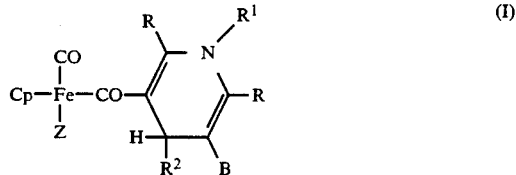

wherein
(i) Cp is either a cyclopentadienyl ligand having the formula $C_5(R^3)_5$ where the $R^3$ groups are independently hydrogen, methyl or ethyl or an indenyl ligand;
(ii) Z is a ligand having the formula $X(R^4)_2(Y)$ wherein X is selected from phosphorus, arsenic or antimony; the $R^4$ groups are independently aryl or aroxy and Y is selected from $-R^5$ $-NHR^5$ and $-OR^5$ wherein $R^5$ is a hydrocarbyl group;
(iii) the R groups are independently hydrogen, halogen or $C_1$ to $C_4$ alkyl;
(iv) $R^1$ is selected from hydrogen, $C_1$ to $C_6$ alkyl, benzyl and $-CO_2R^6$ where $R^6$ is $C_1$ to $C_6$ alkyl;
(v) $R^2$ is selected from hydrogen, $C_1$ to $C_{10}$ alkyl, phenyl and benzyl, and
(vi) B is either R or COY wherein Y is selected from $-NHR^7$, $-OR^7$ and $-SR^7$ where $R^7$ is a hydrocarbyl group.

2. Compounds as claimed in claim 1 wherein Z is a phosphine of formula $P(R^4)_2Y$.

3. Compounds as claimed in claim 2 wherein Y is a chiral $-OR^5$ group.

4. Compounds as claimed in claim 1 wherein R is hydrogen and $R^2$ is selected from hydrogen, methyl ethyl, phenyl and benzyl.

5. Compounds as claimed in claim 4 wherein $R^1$ is selected from hydrogen, $C_1$ to $C_4$ alkyl, benzyl and $-CO_2R^6$ where $R^6$ is $C_1$ to $C_4$ alkyl or phenyl.

6. Compounds as claimed in claim 1 wherein B is COY and $R^7$ is chiral.

7. Compounds as claimed in claim 6 wherein $R^7$ has a chiral centre adjacent to the nitrogen, oxygen or sulphur atom in the group Y.

8. Compounds as claimed in claim 7 wherein $R^7$ is a group having the formula $-C(Ph)(R^8)_2$ where Ph is phenyl and the $R^8$ groups are selected from hydrogen, $-OH$, $-Cl$, $-Br$, $-CN$, $-OR$ and $C_1$ to $C_6$ alkyl or hydroxy alkyl with the proviso that they are non identical.

9. Compounds as claimed in claim 6 wherein $R^7$ is a group having the formula $-(C(R^9)HCH(R^{10})(OH)$ where $R^9$ is $C_1$ to $C_6$ alkyl, phenyl or $CO_2R^{11}$ where $R^{11}$ is $C_1$ to $C_6$ alkyl and $R^{10}$ is hydrogen, $C_1$ to $C_6$ alkyl or phenyl.

10. Single enantiomers of compounds having the formula (I) defined in claim 1 in substantially optically pure form.

11. A process for asymmetrically reducing a carbonyl-containing compound which is prochiral at the carbonyl group, which process comprises the step of contacting the carbonyl-containing compound with a single enantiomer of a compound having the formula:

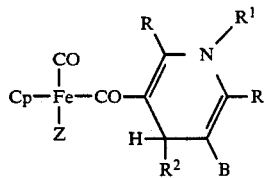

(I)

wherein Cp is either an indenyl ligand or a cyclopentadienyl ligand having the formula $C_5(R^3)_5$ where the $R^3$ groups are independently hydrogen, methyl or ethyl;
Z is a ligand having the formula $X(R^4)_2(Y)$ wherein X is selected from phosphorus, arsenic or antimony;
the $R^4$ groups are independently aryl or aroxy and Y is selected from $-R^5$, $-NHR^5$ and $-OR^5$ wherein $R^5$ is a hydrocarbyl group;
the R groups are independently hydrogen, halogen or $C_1$ to $C_4$ alkyl;
$R^1$ is selected from hydrogen, $C_1$ to $C_6$ alkyl, benzyl and $-CO_2R^6$ where $R^6$ is $C_1$ to $C_6$ alkyl;
$R^2$ is selected from hydrogen, $C_1$ to $C_{10}$ alkyl, phenyl and benzyl, and
B is either R or COY wherein R is as defined above and Y is selected from $-NHR^7$, $-OR^7$ and $-SR^7$ where $R^7$ is a hydrocarbyl group;
at a temperature below 25° C. under conditions where the compound of formula (I) is oxidised.

12. A process as claimed in claim 11 wherein the compound of a formula (I) is one in which B is COY and $R^7$ is chiral.

13. A process as claimed in claim 11 wherein the carbonyl compound is either an acyl or aroyl formate of formula $R^{12}COCO_2R^{13}$ wherein $R^{12}$ is $C_1$ to $C_{10}$ alkyl or phenyl and $R^{13}$ is $C_1$ to $C_{10}$ alkyl.

14. Pyridine derivatives having the formula

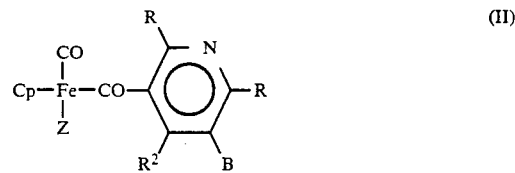

(II)

wherein Cp is either an indenyl ligand or a cyclopentadienyl ligand having the formula $C_5(R^3)_5$ where the $R^3$ groups are independently hydrogen, methyl or ethyl;
the R groups are independently hydrogen, halogen or $C_1$ to $C_4$ alkyl;
$R^2$ is selected from hydrogen, $C_1$ to $C_{10}$ alkyl, phenyl and benzyl and;
B is either R or COY wherein R is as defined above and Y is selected from $-NMR^7$, $-OR^7$ and $OSR^7$ where $R^7$ is a hydrocarbyl group.

15. Quarternised pyridine derivatives having the formula:

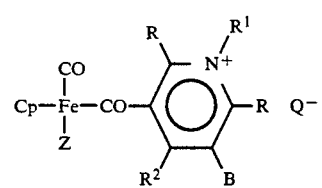

wherein Cp is either an indenyl ligand or a cyclopentadienyl ligand having the formula $C_5(R^3)_5$ where the $R^3$ groups are independently hydrogen, methyl or ethyl;
the R groups are independently hydrogen, halogen or $C_1$ to $C_4$ alkyl;
$R^1$ is selected from hydrogen, $C_1$ to $C_6$ alkyl, benzyl and $-CO_2R^6$ where $R^6$ is $C_1$ to $C_6$ alkyl;
$R^2$ is selected from hydrogen, $C_1$ to $C_{10}$ alkyl, phenyl and benzyl;
B is either R or COY wherein R is as defined above and Y is selected from $-NHR^7$, $-OR^7$ and $SR^7$ where $R^7$ is a hydrocarbyl group; and
$Q^-$ is an anion.

* * * * *